United States Patent
Schultz

(10) Patent No.: US 7,161,678 B2
(45) Date of Patent: Jan. 9, 2007

(54) SYSTEMS AND METHODS FOR DETERMINING THE EXISTENCE OF A VISIBLE PLUME FROM THE CHIMNEY OF A FACILITY BURNING CARBON-BASED FUELS

(75) Inventor: Paul Clarence Schultz, Lakeworth, FL (US)

(73) Assignee: Florida Power and Light Company, Juno Beach, FL (US)

( * ) Notice: Subject to any disclaimer, the term of this patent is extended or adjusted under 35 U.S.C. 154(b) by 594 days.

(21) Appl. No.: 10/158,793

(22) Filed: May 30, 2002

(65) Prior Publication Data

US 2003/0223071 A1    Dec. 4, 2003

(51) Int. Cl.
| | |
|---|---|
| G01N 21/00 | (2006.01) |
| G01N 15/06 | (2006.01) |
| G01N 21/49 | (2006.01) |
| G01N 21/85 | (2006.01) |
| F23N 1/02 | (2006.01) |
| F23N 5/00 | (2006.01) |
| F23N 1/08 | (2006.01) |
| F23N 1/00 | (2006.01) |
| G05D 23/00 | (2006.01) |
| G05D 21/00 | (2006.01) |
| G05D 3/12 | (2006.01) |
| G05D 5/00 | (2006.01) |
| G05D 9/00 | (2006.01) |
| G05D 11/00 | (2006.01) |
| G05D 17/00 | (2006.01) |
| F23C 3/00 | (2006.01) |
| F23K 3/02 | (2006.01) |
| F01N 3/00 | (2006.01) |
| G05B 3/12 | (2006.01) |

(52) U.S. Cl. ............... 356/438; 356/436; 250/573; 431/12; 431/76; 236/14; 236/15 R; 236/15 BD; 60/276; 110/185; 700/274; 700/286

(58) Field of Classification Search ........ 356/436–439, 356/336–343; 250/573–577; 73/23.31, 73/23.32, 31.01, 31.02; 60/276, 670, 660; 431/12, 75, 76, 79, 2, 5, 6, 8, 11–18, 22, 25, 431/62; 236/14, 15 R, 15 BD, 15 E, 15 BR; 110/185–188, 191, 203, 343–345, 341, 342; 700/274, 286, 287, 291, 295; 126/116 R, 126/116 A
See application file for complete search history.

(56) References Cited

U.S. PATENT DOCUMENTS 3,723,047 A * 3/1973 Baudelet de Livois ....... 431/76
4,320,975 A    3/1982 Lilienfeld (Continued)

Primary Examiner—Gregory J. Toatley, Jr.
Assistant Examiner—Gordon J. Stock, Jr.
(74) Attorney, Agent, or Firm—Michael Best & Friedrich LLP

(57) ABSTRACT

Excess oxygen in the combustion process of a facility that burns carbon-based fuels may cause a visible plume in the atmosphere at the stack of the facility. Traditional optical based opacity monitors may be unable to detect this plume or the plume may form at a location downstream from the opacity monitor toward the stack. The present invention discloses methods to utilize common combustion control variables to detect and signal the presence of a visible plume of exhaust gasses. Also disclosed are systems that detect the visible plume and provide a signal so that the combustion process may be manually or automatically adjusted to reduce or eliminate the visible plume.

49 Claims, 7 Drawing Sheets

U.S. PATENT DOCUMENTS

| | | | |
|---|---|---|---|
| 4,362,269 A * | 12/1982 | Rastogi et al. | 236/14 |
| 4,362,499 A * | 12/1982 | Nethery | 431/12 |
| 4,505,246 A | 3/1985 | Nakajima et al. | |
| 4,576,570 A * | 3/1986 | Adams et al. | 431/12 |
| 4,601,273 A | 7/1986 | Kitahara et al. | |
| 4,751,907 A | 6/1988 | Yamamoto et al. | |
| 4,796,587 A | 1/1989 | Nakajima et al. | |
| 5,263,850 A * | 11/1993 | Walker | 431/11 |
| 5,497,332 A * | 3/1996 | Allen et al. | 700/295 |
| 5,511,517 A * | 4/1996 | Perry et al. | 123/1 A |
| 5,605,452 A * | 2/1997 | Robertson et al. | 431/8 |
| 5,656,765 A | 8/1997 | Gray | |
| 5,777,204 A | 7/1998 | Abe | |
| 5,804,700 A | 9/1998 | Kwon et al. | |
| 5,834,624 A | 11/1998 | Nakagawa | |
| 5,901,683 A | 5/1999 | Patel | |
| 5,925,088 A | 7/1999 | Nasu | |
| 5,952,555 A | 9/1999 | Mobius | |
| 6,055,844 A | 5/2000 | Kondo et al. | |
| 6,209,385 B1 | 4/2001 | Silvis | |

\* cited by examiner

SYSTEMS AND METHODS FOR DETERMINING THE EXISTENCE OF A VISIBLE PLUME FROM THE CHIMNEY OF A FACILITY BURNING CARBON-BASED FUELS

FIELD OF THE INVENTION

This invention generally relates to the detection of a visible plume emitted from smokestacks or chimneys of power generating facilities.

BACKGROUND OF THE INVENTION

Opacity monitors are used in facilities wherein exhaust gasses from the combustion of carbon-based fuels can release pollutants into the atmosphere through the facility's chimney. Generally, such opacity monitors utilize an optical detection system that measures opaqueness in the stream of exhaust gasses across the chimney or across an exhaust duct leading to the chimney. The opacity monitor creates an electronic signal that is proportionate, either directly or inversely, to the opaqueness detected in the exhaust stream. This electronic signal is used for automatic or manual control of the facility and the combustion process and for other facility operations or reporting purposes.

Opacity monitors do not have the ability to measure or indicate the appearance of the emission of exhaust gasses from a facility burning carbon-based fuels once such gasses have left the facility's chimney. Opacity, as measured by an opacity monitor, and the curbside appearance of the visual emissions from the chimney can diverge greatly. Combustion quality is one of the largest contributors to the appearance of chimney emissions. When carbon-based fuels are not completely burned because of a lack of the presence of sufficient oxygen during the combustion process, carbon is exported in the exhaust stream out of the chimney. This condition causes high opaqueness of the exhaust stream whereby it is very visible with a black to dark brown color resulting in a high opacity reading from the opacity monitor. This incomplete burning creates a situation where the correlation between the curbside appearance of exhaust gasses and the measured opacity is accurate.

Excess oxygen also affects the combustion process. The presence of excess oxygen beyond what is necessary for complete combustion of the fuel results in a plume being emitted from the facility's chimney. A plume is a visible emission from a facility's chimney that is light gray to white in color that can be very dense or highly opaque under certain conditions. When this heavy plume is present the correlation between the curbside appearance and the measured opacity is poor. The opacity monitor is unable to detect the plume because its formation occurs further down the exhaust stream than where the opacity monitoring device is located. In fact, the plume is generally formed in the atmosphere after the exhaust gasses leave the chimney.

Previous attempts to detect the presence of a visible plume have involved the use of optical detection devices to signal the presence of a smoke plume. U.S. Pat. No. 4,320,975 (Lilienfield), for example, involves a device that operates by measuring the proportion of polarized blue light from the background sky which passes through the plume. Unlike the present invention; however, Lilienfield requires the mounting of a device to "look" through the plume, which may be affected by environmental conditions as well as creating maintenance problems. Moreover, Lilienfield fails to address accuracy issues that may be caused by ambient conditions such as nighttime, cloudy days, etc.

An unsatisfied need therefore exists for systems and methods to determine the presence of an exhaust plume so that such detection can create an electronic signal for the automatic or manual control of the combustion process and to better comply with the United States Environmental Protection Agency's ("EPA's") regulations and guidelines and with other clean-air laws. The opacity monitor is used for this combustion control process but it is overridden when the presence of an exhaust plume is indicated because the two signals (opacity and plume presence) require opposite control action of the same combustion process control variable, excess air. The plume presence signal is developed using combustion related control variable measurements that may be available to a facility's distributed control system ("DCS").

SUMMARY OF THE INVENTION

The invention is based, at least in part, on the discovery that the presence of a visible plume of exhaust gasses at the exhaust stack or chimney of a facility burning carbon-based fuels may be detected using parameters of the combustion process rather than relying upon visible detection of the plume itself. Traditional, optical based opacity monitors may not detect plumes caused by excess oxygen in the combustion process. The present invention detects the conditions that make a plume likely and provides a signal than can be utilized to manually or automatically control the combustion process in order to reduce or eliminate the visible plume.

One aspect of the present invention relates to a system that receives inputs from the combustion process and makes a determination based upon these inputs whether a visible plume of exhaust gasses exist at the facility's stack. In one embodiment, the system receives at least total air and total fuel flow into the combustion chamber of the facility as inputs. The system calculates a ratio of total air flow to total fuel flow and compares this ratio to a predetermined value to determine the presence of a visible plume. Other aspects of the system may incorporate additional inputs such as one or more of opacity from an opacity monitor, oxygen content and carbon monoxide content in the exhaust stream to increase the accuracy of the detection of the plume. These systems may be incorporated into the facility's control system or they may stand alone.

Another aspect of the invention relates to methods for detecting and signaling the presence of a visible plume at the stack of a facility burning carbon-based fuels. These methods rely upon combustion control parameters that may be pre-existing in many power generation facilities. In one embodiment, a method is disclosed to determine the presence of a visible plume from a ratio of the total air and total fuel flow into the combustion chamber of the facility. Other methods may incorporate with the total air flow to total fuel flow ratio additional combustion control parameters such as one or more of opacity from an opacity monitor, oxygen content and carbon monoxide content in the exhaust stream to increase the accuracy of the detection of the plume.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention relates to systems and methods to detect a visible plume of exhaust gasses at the stack of a facility burning carbon-based fuels. Unlike previous systems and methods, the present invention does not attempt to directly detect the plume through only optical means but utilizes combustion control parameters that are generally pre-existing in power generation facilities. Furthermore, the system may readily be incorporated into a facility's existing control system or it may stand alone as a separate module.

Figure 1:
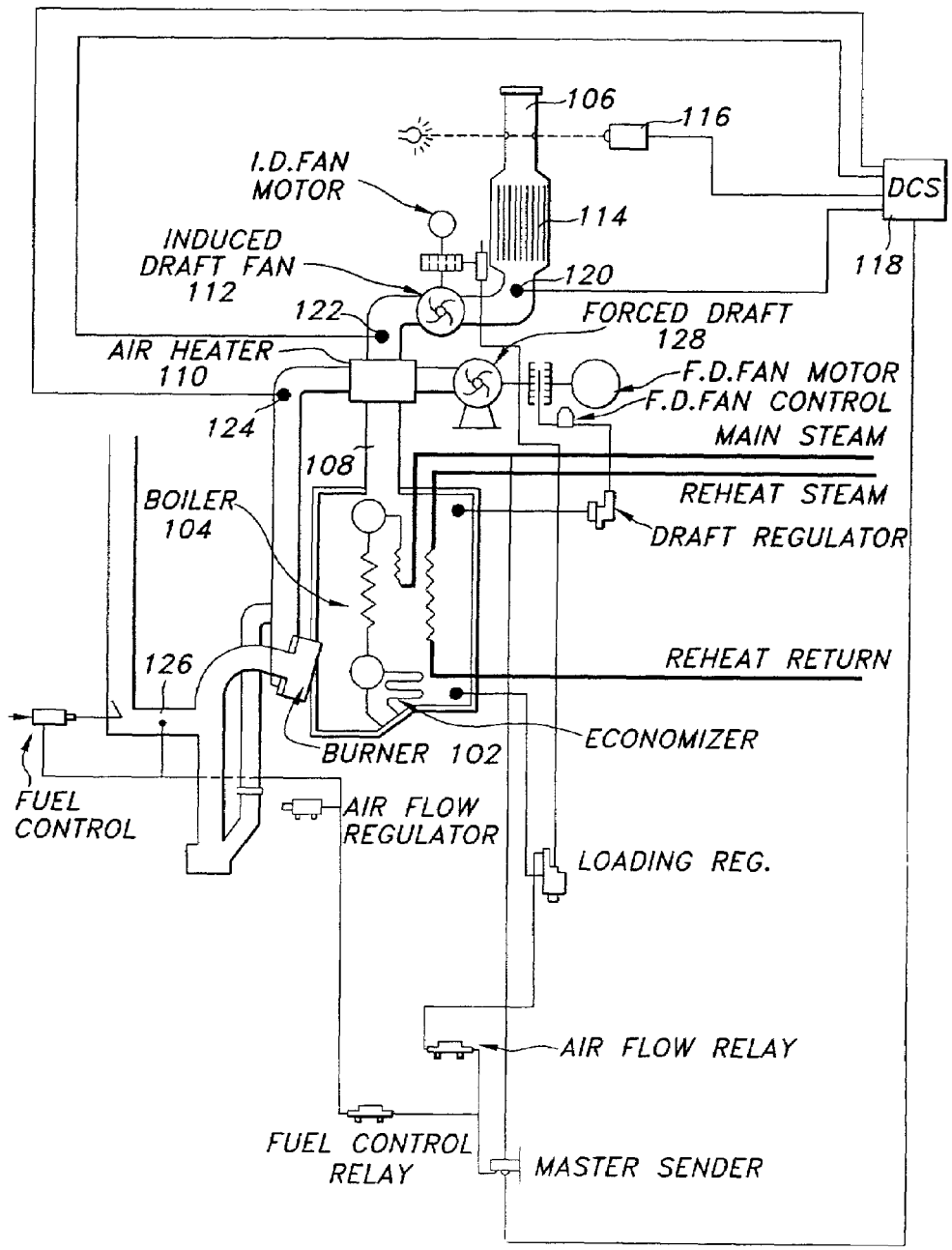
FIG. 1 is an illustrative embodiment of a boiler and combustion control system of a facility utilizing a plume presence monitoring system in accordance with the present invention.

FIG. 1 is a simplified schematic of a power generation facility utilizing an embodiment of a plume presence monitoring system in accordance with the present invention. Referring to FIG. 1, a burner 102 provides fuel and air to a boiler 104 for combustion. The boiler 104 provides steam to a steam turbine which is drivingly connected to an electrical generator which produces electrical power. Exhaust gasses from the combustion are routed from the boiler 104 to the stack 106 where they are emitted to the atmosphere. The exhaust gasses may pass through many devices while being routed from the boiler 104 to the stack 106, including, for example, exhaust ducting 108, an air heater 110, an induced draft fan 112, and an electrostatic precipitator 114, as each of these are well known in the art. The opacity of exhaust gasses in the stack 106 is monitored by an opacity monitor 116, which, generally, measure the opaqueness of the exhaust gasses as they pass by an optical detection device and as such opacity monitors are well known in the art. A signal correlated to the measured opacity ("Instantaneous Opacity") is provided to the facility's Distributed Control System ("DCS") 118. Likewise, carbon monoxide ("CO") monitors 120 and oxygen ("$O_2$") monitors 122, as each are well known in the art, measure the CO and $O_2$, respectively, found in the exhaust gasses as they travel toward the stack 106. These measured CO and $O_2$ quantities are converted into electrical signals by the monitors 120, 122 and the CO signal and $O_2$ signal are received as inputs into the facility's DCS 118.

Devices as are well known in the art monitor the facility's total air 124 and total fuel 126 as is provided to the combustion chamber of the boiler 104. These devices 124, 126 convert the measured quantities of air and fuel, respectively, into electrical signals of total air flow and total fuel flow that are input into the facility's DCS 118. Alternatively, one or both of the values for total air flow and total fuel flow may be calculated by the DCS 118 from other measured parameters such as, for example, the speed of the induced draft fan 112 and/or the speed of a forced draft fan 128, and the weight of the fuel being combusted, respectively.

While FIG. 1 illustrates an embodiment of the invention in a power generation facility with both, induced draft fans 112 and forced draft fans 128, other embodiments of the invention may be employed in power generation facilities having only one or more induced draft fans 112, or in power generation facilities having only one or more forced draft fans 128.

A ratio of the total air flow to total fuel flow is determined. In one embodiment, if the total air flow sufficiently exceeds the total fuel flow, then there is a high likelihood of a visible plume at the stack 106 of the facility and a plume presence signal will be activated. For example, a 300 megawatt ("MW") power generation facility burning No. 6 fuel oil in its boiler may have a minimum threshold value for the total air flow to total fuel flow ratio of preferably 1.02. In other words, in this example, if the total air flow to total fuel flow ratio equals or exceeds approximately 1.02, this embodiment of the invention will signal the presence of a visible plume at the stack 106 of the facility. To reduce the likelihood of this embodiment of the system providing a false plume presence signal, other combustion related control variables may be introduced in the system. For example, in an embodiment of the present invention, the likelihood of a false plume presence signal is greatly reduced in a 300 MW power generation facility burning No. 6 fuel oil in its boiler, for example, if, in addition to the total air flow to total fuel flow ratio being greater than or equal to preferably 1.02, the $O_2$ in its exhaust gasses, as measured by the $O_2$ monitor 122, exceeds a threshold limit that is a function of the current MW demand of the generator (i.e., the amount of electrical power currently being produced by the electrical generator); if the CO measured in the exhaust gasses as measured by the CO monitor 120 is less than preferably 100 parts per million ("ppm"); and if the instantaneous opacity as measured by the opacity monitor 116 is, for example, less than or equal to preferably 20 percent. These additional $O_2$ and CO signals are provided as inputs to the DCS 118 in an embodiment of the present invention and, if the conditions indicated above are present, the system will provide a plume presence signal that has a much greater likelihood of correctly signaling the presence of a plume than if the system relied only upon the total air flow to total fuel flow ratio.

The embodiment of the system illustrated in FIG. 1 can be used to manually or automatically adjust the combustion process in the event the presence of a plume at the stack 106 of the power generation facility is indicated by the a plume presence signal from the system. The signal can be used to alert an operator to adjust any one or any combination of fuel flow, induced draft fans 112, or forced draft fans 128 to reduce or eliminate the visible plume. Likewise, the plume presence signal can be utilized by the DCS 118 to automatically adjust any one of or any combination of fuel flow, induced draft fans 112, or forced draft fans 128 to reduce or eliminate the visible plume.

Figure 2:
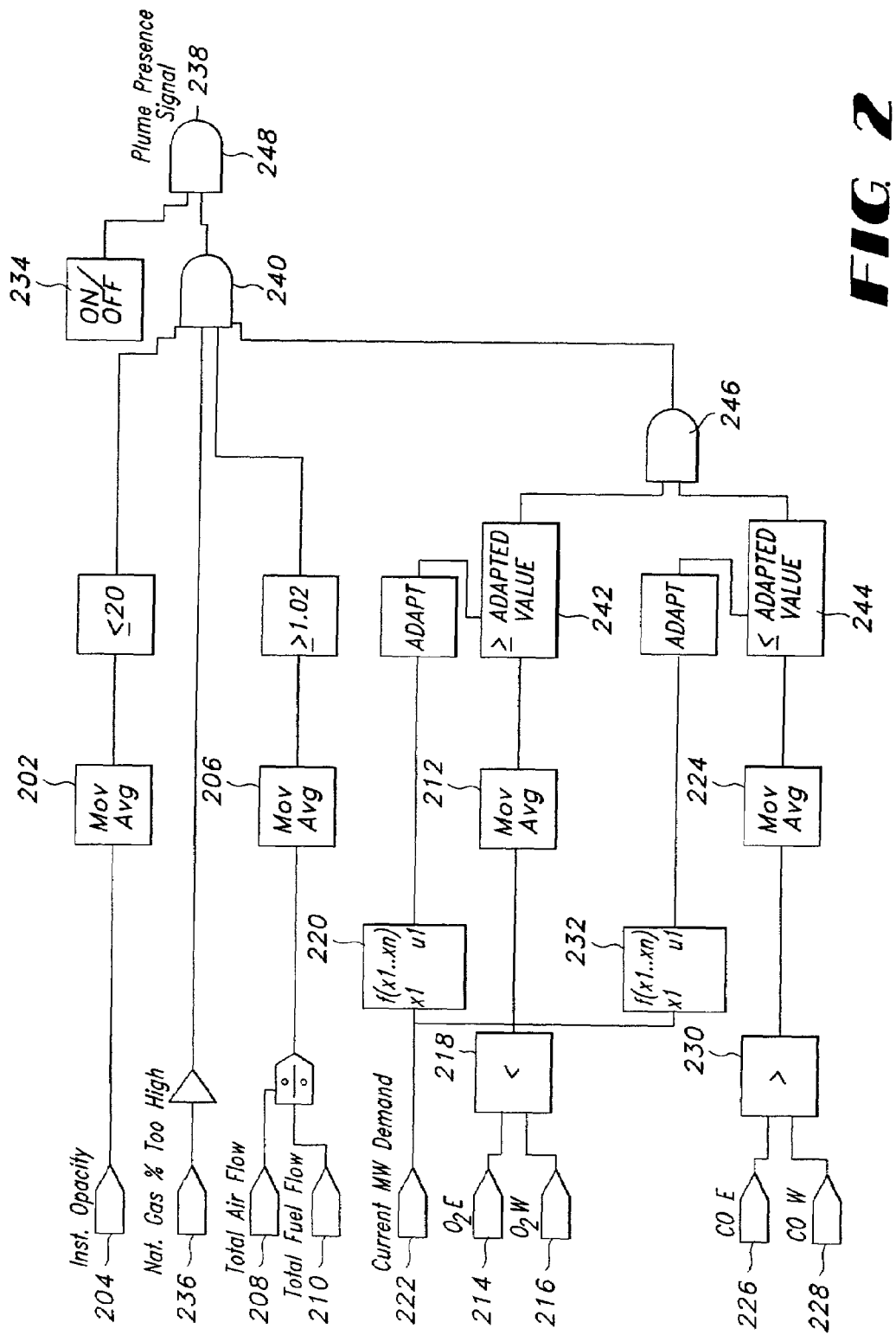
FIG. 2 is a plume presence circuit, in accordance with an embodiment of the present invention, for use in a dual-fuel power generation facility burning either No. 6 fuel oil and/or natural gas in its boiler.

FIG. 2 illustrates an embodiment of a logic circuit for detecting and signaling the presence of a visible plume at the chimney or stack of a dual-fuel power generation facility that is capable of combusting No. 6 fuel oil and/or natural gas in its boiler. This circuit provides a logical Boolean output of "TRUE" or a "1" if a visible plume is present at the stack of the facility. This output can be used to automatically or manually adjust the combustion process in order to eliminate or reduce the visible plume.

Generally, and as explained in detail below, this circuit operates by determining if a moving average 202 of the instantaneous opacity 204 of the exhaust gasses is less than or equal to a predetermined value, such as approximately 20 percent in the present embodiment; if a moving average 206 of the total air flow 208 into the boiler divided by the total fuel flow 210 into the boiler is greater than or equal to a predetermined value, such as approximately 1.02 in the present embodiment; if a moving average 212 of the lowest $O_2$ percentage reading 214, 216, as determined by comparing 218 one or more $O_2$ inputs 214, 216, as such inputs are obtained from the exhaust gas stream of the facility, is greater than a maximum normal $O_2$ percentage, as such maximum normal $O_2$ percentage is determined as a function 220 of the current MW demand 222 of the facility; and, if the moving average 224 of the greatest CO percentage reading 226, 228, as determined by comparing 230 one or more CO inputs 226, 228, as such inputs are obtained from the exhaust gas stream of the facility, is less than a minimum normal CO percentage, as such minimum normal CO is determined as a function 232 of the current MW demand 222 of the facility. If all of the above-recited elements are present, if the circuit is "ON" 234 and if the facility is not burning more than a set percentage of natural gas 236, the circuit will signal the presence of a visible plume 238 at the stack of the facility.

The power generating facility employing the exemplary circuit in FIG. 2 is capable of concurrently burning natural gas and fuel oil, or burning each fuel exclusively. Natural gas is a "clean burning" fuel in that it is highly unlikely to produce a visible plume during combustion. In the circuit illustrated in FIG. 2, if the ratio of natural gas to total fuel (natural gas and fuel oil) exceeds a predetermined limit, then the circuit will not signal the presence of a visible plume because the likelihood of a visible plume decreases as the ratio of natural gas to total fuel increases. This natural gas cutoff is controlled by the input "Nat. Gas % Too High" 236 as indicated on FIG. 2. In this illustrative circuit of FIG. 2, if a predetermined value, such as approximately 20 percent or more of the total fuel being combusted in the present embodiment is natural gas, the circuit will not signal the presence of a visible plume 238 because it is highly unlikely that a visible plume will be present when burning natural gas at concentrations equal to or greater than this predetermined value. This "Nat. Gas % Too High" 236 input is illustrative of the flexibility and adaptability of this circuit, is not a required input for the circuit, and is obviously not necessary in facilities that burn only one fuel. Furthermore, the circuit can be activated or deactivated either automatically or manually as indicated by the "ON/OFF" input 234 of FIG. 2.

The exemplary circuit illustrated in FIG. 2, as well as other embodiments of the invention, may be incorporated into a mechanism consisting of a control system of a facility utilizing the invention. Such a mechanism may consist of one, or a combination of, software, hardware, firmware, DCS, stand-alone devices and components, manual calculations and/or data entry, etc. For example, the logic of this embodiment of the circuit may be programmed into a facility's DCS and utilize pre-existing DCS inputs such as instantaneous opacity 204, total air flow 208, total fuel flow 210, $O_2$ inputs 214, 216, current MW demand 222, CO inputs 226, 228, etc., perform logic operations upon the inputs, and produce or not produce a plume presence signal 238, depending upon the outcome of the logic operations. Other embodiments of the invention may utilize mechanisms that exist independently of a facility's control system or are only partially integrated into the facility's control system. Such a mechanism may consist of one, or a combination of, software, hardware, firmware, a facility's DCS, a separate DCS, standalone components and devices, manual calculations and/or data entry, etc. For example, the logic of the exemplary circuit in FIG. 2 or in other embodiments of the invention may be incorporated into a separate control module wherein the control module receives inputs such as instantaneous opacity 204, total air flow 208, total fuel flow 210, $O_2$ inputs 214, 216, current MW demand 222, CO inputs 226, 228, etc., performs logic operations upon the inputs, and does or not produce a plume presence signal 238, depending upon the outcome of the logic operations.

Referring now to the exemplary embodiments of the invention in FIGS. 1 and 2, an opacity monitor 116, preferably an optical-based opacity monitor as is well-known in the art, detects the opacity of the exhaust gasses at a point upstream from the outlet of the stack 106. The opacity monitor 116 sends an instantaneous opacity signal 204 to the facility's DCS 118, and the instantaneous opacity signal 204 is utilized as an input to the plume presence logic circuit of FIG. 2. In this embodiment, the plume presence logic circuit of FIG. 2 is a part of the DCS 118, however, the plume presence logic circuit may be a part of any control or processor system or may, as described above, be a separate, stand-alone device. A moving average 202 is taken of the instantaneous opacity 204 input. The average instantaneous opacity 204 must be less than or equal to a predetermined value, such as approximately 20 percent in the present embodiment, before the circuit in FIG. 2 will trigger a Plume Presence Signal 238.

A component of the embodiment of the plume presence circuit of FIG. 2 is determining the total air flow 208 to total fuel flow 210 ratio. Total air flow 208 is a measurement of the amount of air flowing into the combustion chamber of the boiler 104 during the power generation process. It is generally a function of the forced draft 128 and/or the induced draft fans 112 of a typical power generation facility. Total fuel flow 210 is a measurement of the fuel flowing into the combustion chamber of the boiler 104 during the power generation process. In the embodiment illustrated in FIG. 2, the fuel is either natural gas, fuel oil, or a combination of the two, but in other power generation facilities the fuel may be coal, coke, heavy oils, petroleum distillates, synthetic fuels, wood, bark, shredded tires, trash, or any other combustible material and any combination of these. Although these fuels may be measured in various units, the DCS 118 generally converts the fuel flow into units compatible with the air flow.

The moving average 206 of the ratio of the total air flow 208 to total fuel flow 210 must be greater than or equal to a predetermined value, such as approximately 1.02 in the present embodiment, in order to detect the presence of a visible plume with the exemplary circuit illustrated in FIG. 2. A Boolean operator of "TRUE" is sent to an and gate 240 if the ratio of the total air flow 208 to total fuel flow 210 is greater than or equal to the predetermined value. This predetermined value is empirically determined by visually monitoring the stack 106 of the power generation facility at various ratios of total air flow 208 and total fuel flow 210 and recording the values of total air flow 208 and total fuel flow 210 when a visible plume either is, or is not, present. The ratio may vary according to the fuel burned at the power generation facility.

Figure 3:
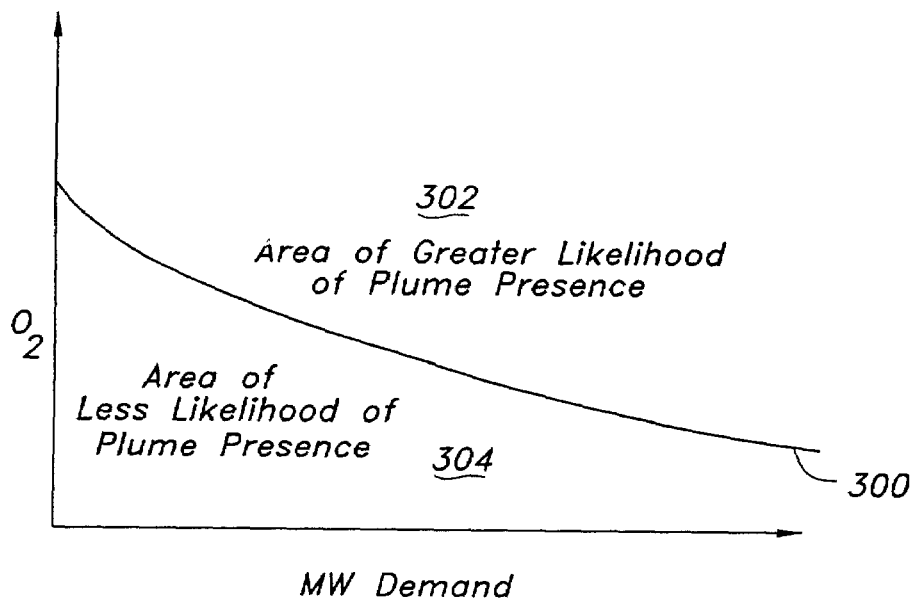
FIG. 3 is an illustrative graph, in accordance with an embodiment of the present invention, illustrating an exemplary curve for determining a level of $O_2$ in exhaust gasses from a power generation facility for which there is a likelihood of the presence of a visible plume.

The power generation facility utilizing the exemplary circuit illustrated in FIG. 2 has two forced draft fans 128 and two induced draft fans 112 that provide air to the combustion chamber in the boiler 104 and create a draft through the boiler 104 and into the stack 106, respectively, although other power generation facilities may have only one or more forced draft fans 128, only one or more induced draft fans 112, or a combination of one or more forced draft fans 128 and one or more induced draft fans 112. The $O_2$ content of the exhaust gasses passing through each of the induced draft fans 112 is monitored and provided as inputs to the DCS 118. $O_2$ E 214 is the $O_2$ content in the exhaust gasses passing through the east induced draft fan 112 and $O_2$ W 216 is the $O_2$ content of the exhaust gasses passing through the west induced draft fan 112. The lowest of these two $O_2$ inputs 214, 216 is determined by the $O_2$ comparison block 218 and the moving average 212 of the lowest $O_2$ value is determined. This moving average 212 of the lowest $O_2$ reading must exceed a lower threshold limit as such lower limit is determined as a function of the current MW demand 222 of the facility. Relating the minimum $O_2$ level where plume presence is likely as a function of the current MW demand 222 of the facility is determined empirically by recording the $O_2$ level over various ranges of MW demand 222 over time and for numerous combinations of $O_2$ and MW demand 222, and visually determining if a plume is present at the stack 106 of the power generation facility at the recorded $O_2$ level and MW demand 222. This empirical analysis then allows a curve to be determined whereby if the $O_2$ level at a certain MW demand exceeds the curve, then there is a likelihood that a plume will be present at the stack 106 of the power generation facility. FIG. 3 is an illustrative example of the appearance of such a curve 300, as such curve 300 may be determined from empirical analysis. In the illustrative example of FIG. 3, if the $O_2$ level at a certain MW Demand 222 is on the curve 300, or in the area above the curve 302, then there is a greater likelihood of the presence of a visible plume at the stack 106 of the power generation facility than if the $O_2$ level at the same MW Demand 222 is in the area below the curve 304. Logically, as illustrated in the exemplary circuit of FIG. 2, the threshold minimum for $O_2$ is set as a function of current MW demand 222 by the $O_2$ MW function block 220.

Figure 4:
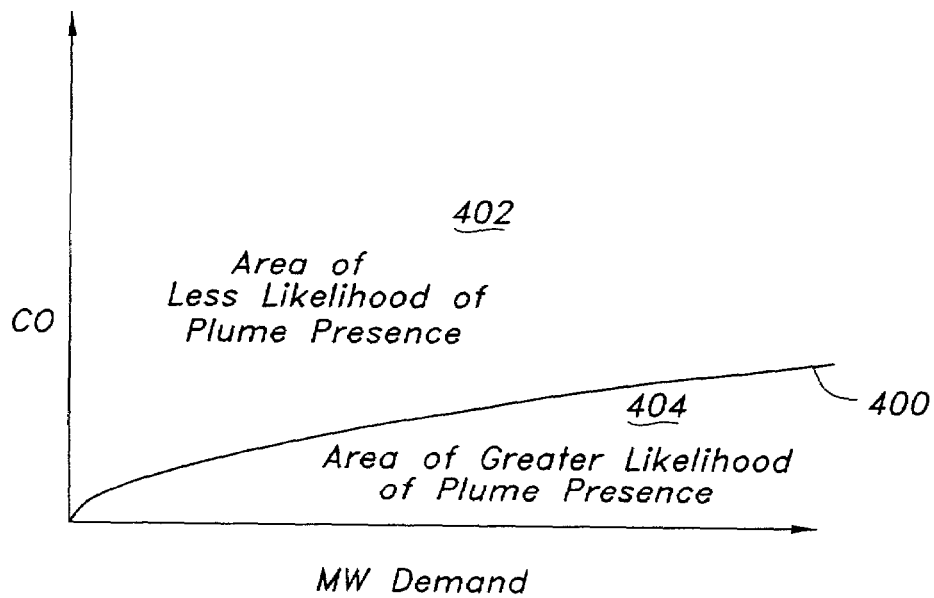
FIG. 4 is an illustrative graph, in accordance with an embodiment of the present invention, illustrating an exemplary curve for determining a level of CO in exhaust gasses from a power generation facility for which there is a likelihood of the presence of a visible plume.

Likewise, the CO content of the exhaust gasses passing through each of the induced draft fans 112 is monitored and provided as inputs to the DCS 118. CO E 226 is the CO content in the exhaust gasses passing through the east induced draft fan 112 and CO W 228 is the CO content of the exhaust gasses passing through the west induced draft fan 112. The higher of these two CO inputs 226, 228 is determined by the CO comparison block 230 and the moving average 224 of this higher CO value is determined. This moving average 224 of the highest CO reading must be less than an upper threshold limit as such upper limit is determined as a function of the current MW demand 222 of the facility. Relating the maximum CO level where plume presence is likely as a function of the current MW demand 222 of the facility is determined empirically by recording the CO level over various ranges of MW demand 222 over time and for numerous combinations of CO and MW demand 222, and visually determining if a plume is present at the stack 106 of the power generation facility at the numerous recorded CO levels and MW demands 222. This empirical analysis then allows a curve to be determined whereby if the CO level at a certain MW demand exceeds the curve, then there is a lessened likelihood that a plume will be present at the stack 106 of the power generation facility. FIG. 4 is an illustrative example of the appearance of such a curve 400, as such curve 400 may be determined from empirical analysis. In the illustrative example of FIG. 4, if the CO level at a certain MW Demand 222 is in the area above the curve 402, then there is a lesser likelihood of the presence of a visible plume at the stack 106 of the power generation facility than if the CO level at the same MW Demand 222 is on the curve 400, or in the area below the curve 404. Logically, as illustrated in the exemplary circuit of FIG. 2., the threshold maximum for CO is set as a function of current MW demand 222 by the CO MW function block 232. One of ordinary skill in the art will readily recognize that the $O_2$ 122 and CO monitors 120 may be located anywhere in the exhaust gas stream before the gasses exit the stack 106.

The moving averages 212, 224 of the $O_2$ 214, 216 and CO 226, 228 inputs are compared to their threshold levels at the process comparison blocks 242 and 244, respectively. The thresholds for the process comparison blocks 242, 244 are set as a function of current MW demand 222. If the moving average 212 of the lowest $O_2$ input 214, 216 is greater than or equal to its threshold, as compared to such threshold by the $O_2$ process comparison block 242, then a Boolean "TRUE" output is provided by the $O_2$ process comparison block 242. Likewise, if the moving average 224 of the highest CO input 226, 228 is less than or equal to its threshold, as compared to such threshold by the CO process comparison block 244, then a Boolean "TRUE" output is provided by the CO process comparison block 244. The outputs of the $O_2$ process comparison block 242 and the CO process comparison block 244 are each provided as inputs to an and gate 246. The output of the and gate 246 is provided as an input to the and gate 240. Though utilizing three logical and gates, one of ordinary skill in the art will readily recognize that the exemplary circuit illustrated in FIG. 2 may be configured with as few as one logical and gate. Furthermore, while FIG. 2 illustrates the use of moving averages 202, 206, 212, and 224, for several inputs, one of ordinary skill in the art will readily recognize that such averages are provided only to increase the stability of the exemplary circuit illustrated in FIG. 2, and that the circuit and its various inputs may be configured with or without such moving averages.

In an embodiment of the invention as illustrated in the exemplary circuit of FIG. 2, if the logical signals that are input to and gate 240 are "TRUE", that is if the total air flow 208 to total fuel flow 210 ratio is equal to or greater than a predetermined value such as approximately 1.02; if the lowest $O_2$ reading 214, 216 is greater than or equal to a minimum threshold that is determined as a function of the current MW demand 222 of the facility; if the highest CO reading 226, 228 is less than or equal to a maximum threshold that is determined as a function of the current MW demand 222 of the facility; and if the instantaneous opacity 204 of the facility is less than another predetermined value such as approximately 20 percent, and if the circuit "ON" signal 234 is "TRUE," then the circuit illustrated in FIG. 2 will provide a Boolean "TRUE" output at an and gate 248 which shall constitute a plume presence signal 238 for a power generation facility burning No. 6 fuel oil in its boiler.

It is to be recognized that although FIGS. 1 and 2 are illustrative of embodiments of the invention applied in a power generation facility that utilizes a boiler to provide steam to a steam turbine that drives an electrical power generator, these embodiments or other embodiments of the invention can be applied in combustion turbine engines, diesel engines, gasoline engines, and other engines or facilities where the combustion of carbonbased fuels may lead to the presence of a visible plume. Embodiments of the invention can also be applied in facilities that are not used for electrical power generation, such as pulp and paper mills, refineries, and other process facilities where carbon-based fuels are burned. The invention would be particularly useful in a combustion turbine power generation facility that utilizes a petroleum product or by-product as a fuel.

Figure 5:
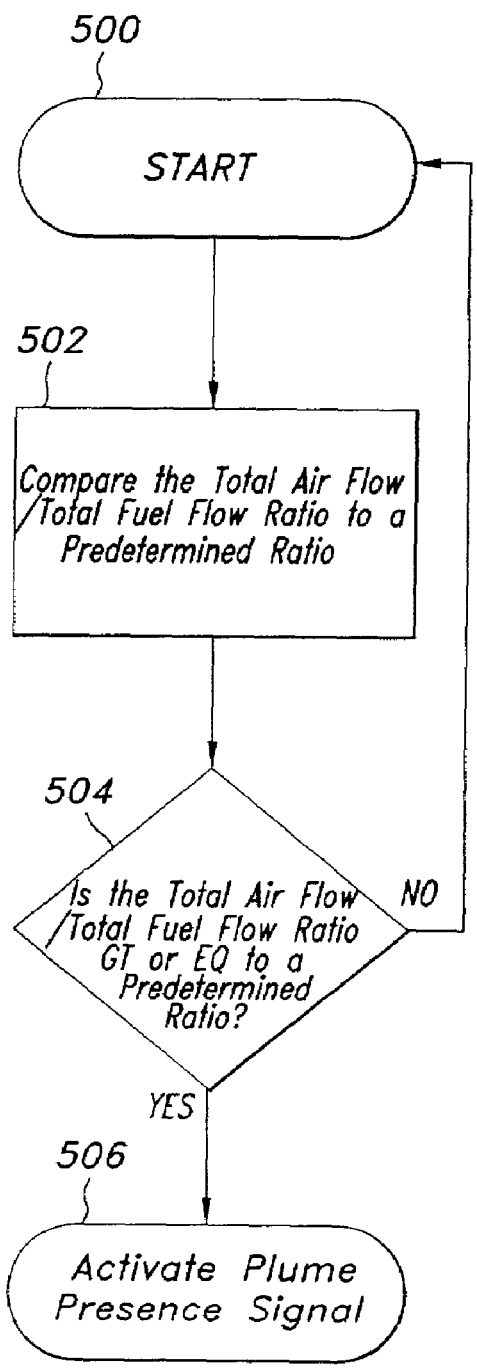
FIG. 5 is a flow chart illustrating an exemplary method to determine the presence of a visible plume at the chimney or stack of a facility burning carbon-based fuels in accordance with the present invention.

FIG. 5 is a flow chart illustrating an exemplary method to determine the presence of a visible plume at the chimney or stack of a facility burning carbon-based fuels in accordance with the present invention. In Step 502 of this embodiment, the ratio of the total air flow entering the combustion chamber of a boiler to the total fuel flow that is entering the boiler is compared to a predetermined value. In Step 504, if the ratio of Step 502 is greater than or equal to the predetermined value, then a plume presence signal is activated in Step 506. If the ratio of Step 502 is less than the predetermined value, then the process returns to its beginning (Step 500) and begins the process anew. For example, in an embodiment of the invention, if the ratio of total air flow to total fuel flow is greater than or equal to approximately 1.02 in a boiler burning No. 6 fuel oil, a plume presence signal 238 will be provided.

Figure 6:
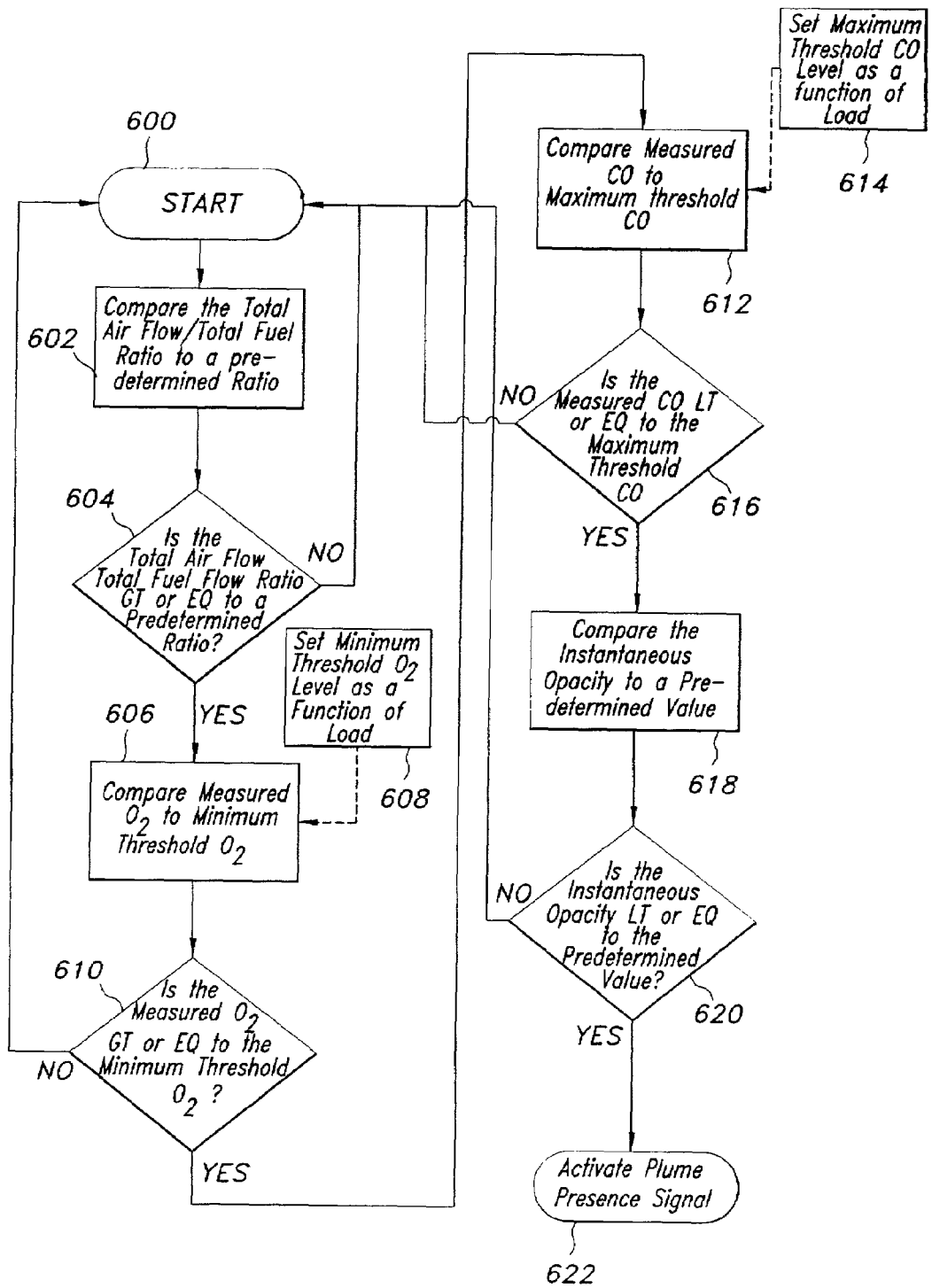
FIG. 6 is a flow chart illustrating a second exemplary method to determine the presence of a visible plume at the stack of a facility burning carbon-based fuels in accordance with the present invention.

FIG. 6 is a flow chart illustrating a second exemplary method to determine the presence of a visible plume at the stack of a facility burning carbon-based fuels in accordance with the present invention. In Step 602 of this embodiment, the ratio of the total air flow entering the combustion chamber of a boiler to the total fuel flow that is entering the boiler to a predetermined value. In Step 604, if the ratio of Step 602 is greater than or equal to the predetermined value, then the process continues on to Step 606. If the ratio of Step 602 is less than the predetermined value, then the process returns to its beginning (Step 600) and begins anew.

In Step 606, a measured $O_2$ value of the exhaust gasses from the combustion is compared to a minimum threshold $O_2$ value. This minimum threshold $O_2$ level is established in Block 608 as a function of the rate of combustion which is proportional to the steam being produced by the boiler and the load on the boiler. In Step 610, if the measured $O_2$ value is greater than or equal to the minimum threshold $O_2$ (as established by Block 608), then the process continues on to Step 612, otherwise if the measured $O_2$ value is less than the minimum threshold $O_2$ value, then the process returns to its beginning (Step 600) and begins anew.

In Step 612, a measured CO value of the exhaust gasses from the combustion is compared to a maximum threshold CO value. This maximum threshold CO level is established in Block 614 as a function of the rate of combustion which is proportional to the steam being produced by the boiler and the load on the boiler. In Step 616, if the measured CO value is less than or equal to the maximum threshold CO (as established by Block 614), then the process continues on to Step 618, otherwise if the measured CO value is greater than the maximum threshold CO value, then the process returns to its beginning (Step 600) and begins anew.

In Step 618, a measured instantaneous opacity value of the exhaust gasses produced by the combustion is compared to a second predetermined value. In Step 620, if the measured instantaneous opacity is less than or equal to the second predetermined value, the process moves on to Step 622 and signals the presence of a visible plume. If the measured instantaneous opacity in Step 620 is greater than the second predetermined value, then the process returns to its beginning (Step 600) and begins anew.

Figure 7:
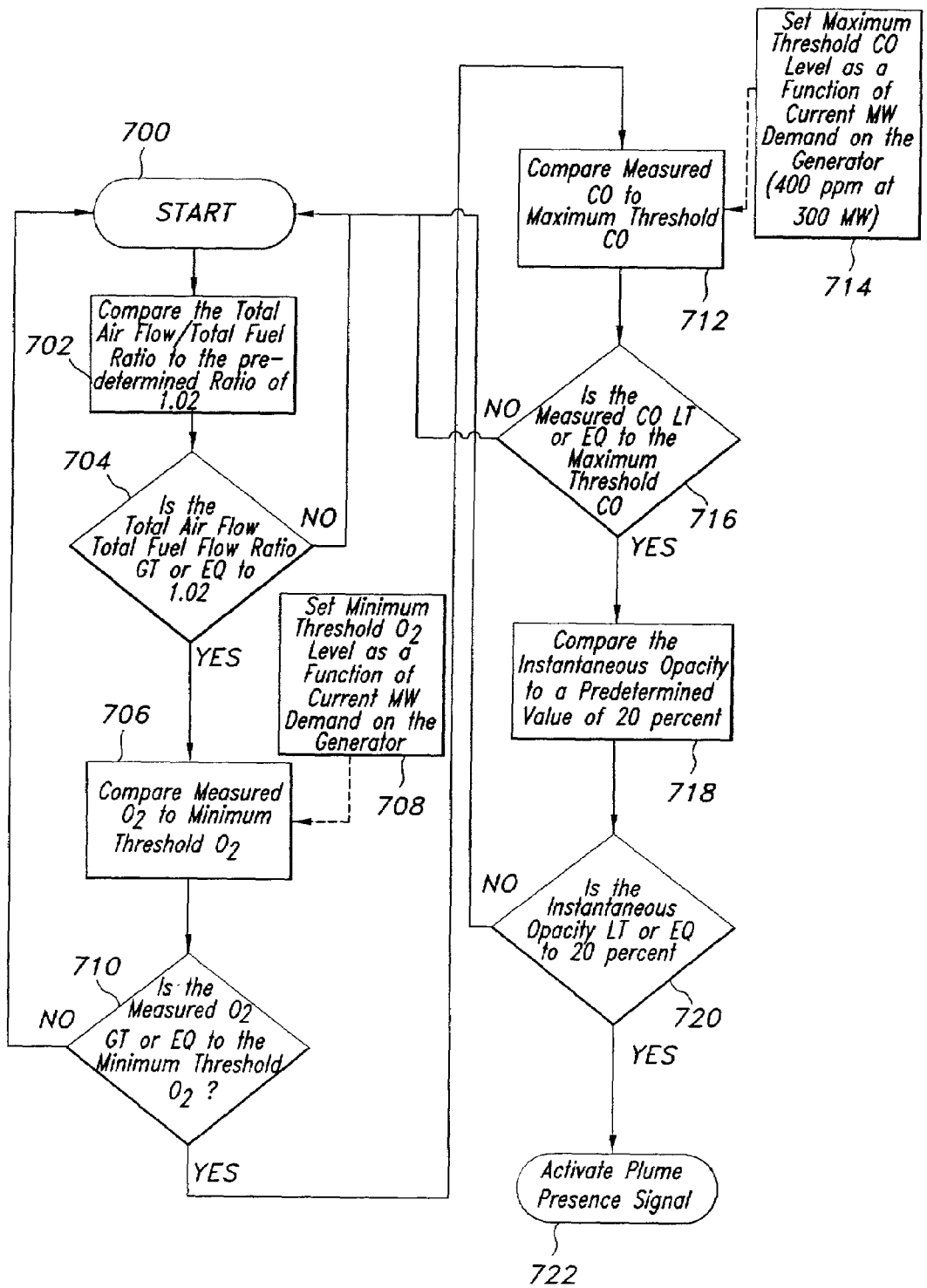
FIG. 7 is a flow chart illustrating the second exemplary method to determine the presence of a visible plume at the stack of a power generation facility burning carbon-based fuels in accordance with the present invention at a power generating facility that combusts No. 6 fuel oil as its primary fuel in its boiler.
Figure 8:
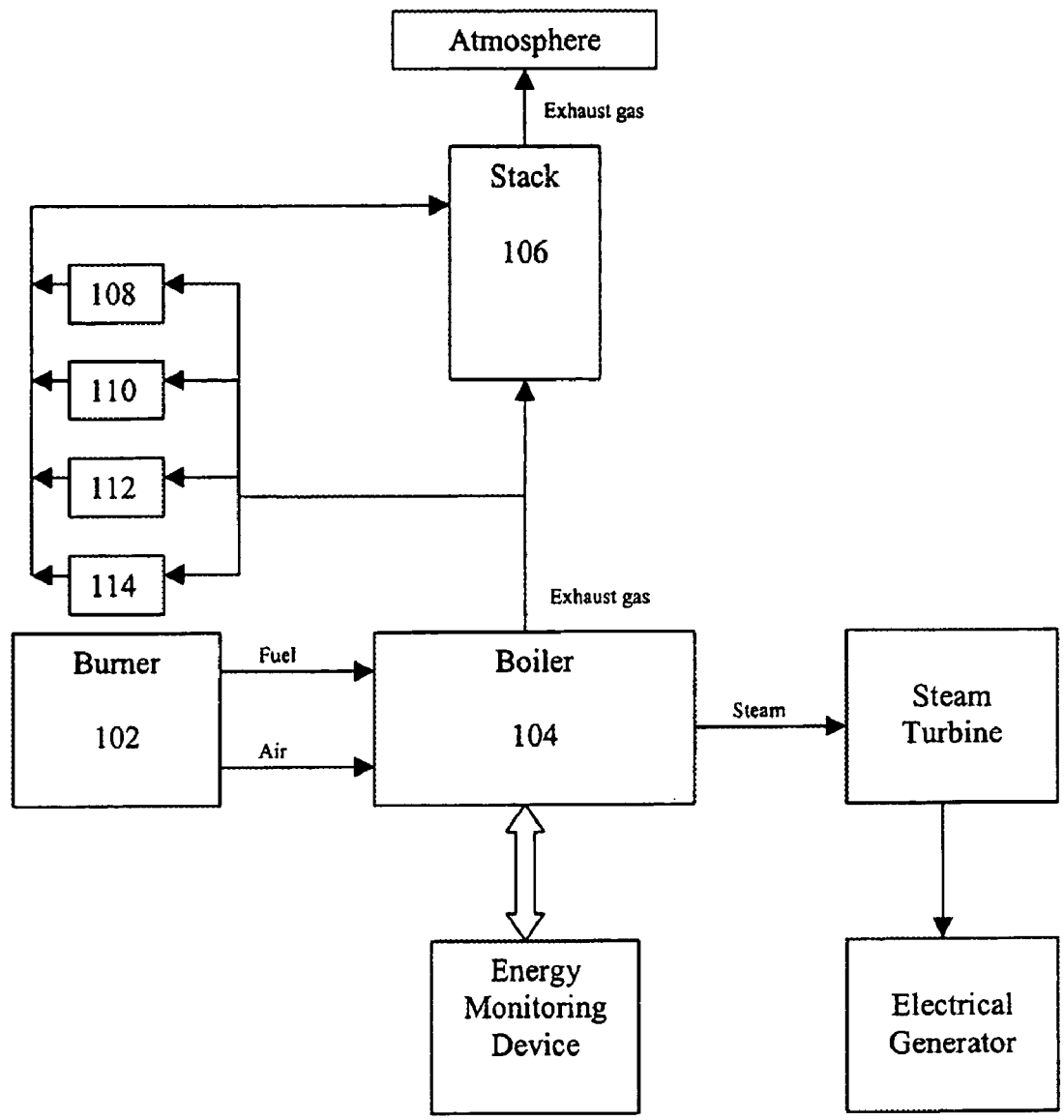
FIG. 8 is schematic illustration of a stem turbine, an electrical generator, and an energy monitoring device for use with a plume presence monitoring system according to one embodiment of the invention.

FIG. 7 is a flow chart illustrating the second exemplary method to determine the presence of a visible plume at the stack of a power generation facility burning carbon-based fuels in accordance with the present invention. The exemplary power generation facility illustrated in this embodiment of FIG. 7 has a 300 MW generator driven by a steam turbine and the facility burns No. 6 fuel oil in its boiler. In Step 702 of this embodiment, the ratio of the total air flow entering the combustion chamber of a boiler to the total fuel flow that is entering the boiler to a predetermined value, such as approximately 1.02, in this embodiment. In Step 704, if the ratio of Step 702 is greater than or equal to the predetermined value of approximately 1.02, then the process continues on to Step 706. If the ratio of Step 702 is less than the predetermined value of approximately 1.02, then the process returns to its beginning (Step 700) and begins anew.

In Step 706, a measured $O_2$ value of the exhaust gasses from the combustion is compared to a minimum threshold $O_2$ value. This minimum threshold $O_2$ level is established in Block 708 as a function of the rate of combustion which is proportional to the steam being produced by the boiler and the load on the boiler (and, in this instance, the current MW demand of the electrical generator that is driven by the steam turbine). In Step 710, if the measured $O_2$ value is greater than or equal to the minimum threshold $O_2$ (as established by Block 708), then the process continues on to Step 712, otherwise if the measured $O_2$ value is less than the minimum threshold $O_2$ value, then the process returns to its beginning (Step 700) and begins anew.

In Step 712, a measured CO value of the exhaust gasses from the combustion is compared to a maximum threshold CO value. This maximum threshold CO level is established in Block 714 as a function of the rate of combustion which is proportional to the steam being produced by the boiler and the load on the boiler (and, in this instance, the current MW demand of the electrical generator that is driven by the steam turbine). In this embodiment of the invention utilized on a 300 MW power generation facility that burns No. 6 fuel oil in its boiler, the maximum threshold CO level at 300 MW demand is approximately 100 ppm. In Step 716, if the measured CO value is less than or equal to the maximum threshold CO (as established by Block 714), then the process continues on to Step 718, otherwise if the measured CO value is greater than the maximum threshold CO value, then the process returns to its beginning (Step 700) and begins anew.

In Step 718, a measured instantaneous opacity value of the exhaust gasses produced by the combustion is compared to a second predetermined value. In this embodiment of the invention utilized on a 300 MW power generation facility that burns No. 6 fuel oil in its boiler, the second predetermined value is approximately 20 percent. In Step 720, if the measured instantaneous opacity is less than or equal to the second predetermined value, the process moves on to Step 722 and signals the presence of a visible plume. If the measured instantaneous opacity in Step 720 is greater than the second predetermined value, then the process returns to its beginning (Step 700) and begins anew.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system that determines the presence of a visible plume of exhaust gasses at a power generation facility with a stack, wherein the system comprises:
   an air flow monitor that measures total air flowing into a combustion chamber during combustion;
   a fuel flow monitor that measures total fuel flowing into the combustion chamber during combustion; and
   a control system for excess air conditions that determines a plume presence signal including a ratio of total air flow as measured by the air flow monitor and the total fuel flow as measured by the fuel flow monitor and compares the ratio to a first plume presence value and produces a first input into the determination of the presence of a visible plume if the ratio is at least equal to the first plume presence value.

2. The system of claim 1, wherein the combustion chamber combusts No. 6 fuel oil.

3. The system of claim 2, wherein the first plume presence value is 1.02.

4. The system of claim 1, further comprising:
   an exhaust path through which exhaust gasses are routed from the combustion chamber to the stack during combustion;
   an opacity monitor located in one of the stack and the exhaust path that determines the opacity of exhaust gasses passing through one of the exhaust path and stack; and
   wherein the control system compares the opacity of the exhaust gasses as determined by the opacity monitor to a second plume presence value to produce a second input into the determination of the presence of a visible plume if the first input has been produced.

5. The system of claim 4, wherein the control system signals the presence of a visible plume at the stack of the facility if the ratio and the opacity of the exhaust gasses indicate a visible plume.

6. The system of claim 5, wherein the combustion chamber combusts No. 6 fuel oil.

7. The system of claim 6 wherein the first plume presence value is 1.02 and the second plume presence value is 20 percent.

8. The system of claim 1, further comprising:
   an exhaust path through which exhaust gasses are routed from the combustion chamber to the stack during combustion;
   a carbon monoxide monitor located in one of the stack and the exhaust path that determines the carbon monoxide content of the exhaust gasses;
   an oxygen monitor located in one of the stack and the exhaust path that determines the oxygen content of the exhaust gasses; and
   wherein the control system compares the carbon monoxide content of the exhaust gasses as determined by the carbon monoxide monitor to a second plume presence value and compares the oxygen content of the exhaust gasses as determined by the oxygen monitor to a third plume presence value to produce a second input and a third input input, respectively, into the determination of the presence of a visible plume only if the first input has been produced.

9. The system of claim 8, wherein the control system signals the presence of a visible plume if the ratio, the carbon monoxide content of the exhaust gasses, and the oxygen content of the exhaust gasses indicate a visible plume.

10. The system of claim 9, further comprising a boiler to provide steam to a steam turbine; the boiler heated by heat from combustion of a fuel in the combustion chamber of the boiler; the steam turbine driven by steam from the boiler; the steam turbine drivingly connected to an electrical power generator for the generation of electrical energy; and an energy monitoring device for measuring the electrical energy being generated by the generator.

11. The system of claim 10, wherein the control system continuously determines the second plume presence value and the third plume presence value as functions of the electrical energy being generated by the generator, as such electrical energy is measured by the energy monitor, and as a function of the fuel only if the first input has been produced.

12. The system of claim 11, wherein the fuel is No. 6 fuel oil.

13. The system of claim 12 wherein the first plume presence value is 1.02.

14. The system of claim 1, wherein the first plume presence value is generated from the ratio and at least one of carbon monoxide content of the exhaust gasses, oxygen content of the exhaust gasses, speed of an induced draft fan, weight of fuel being combusted, amount of natural gas being used, type of fuel being used, and electricity demand of the facility.

15. A system that determines the presence of a visible plume of exhaust gasses at a power generation facility with a stack, wherein the system comprises:
   an exhaust path through which exhaust gasses are routed from a combustion chamber to the stack during combustion;
   an air flow monitor that measures air flowing into the combustion chamber during combustion;
   a fuel flow monitor that measures fuel flowing into the combustion chamber during combustion;
   an opacity monitor located in one of the stack and the exhaust path that determines the opacity of exhaust gasses passing through one of the stack and exhaust path;
   a carbon monoxide monitor located in one of the stack and the exhaust path that determines the carbon monoxide content of the exhaust gasses;

an oxygen monitor located in one of the stack and the exhaust path that determines the oxygen content of the exhaust gasses; and a control system for excess air conditions that determines a plume presence signal including a ratio of total air flow as measured by the air flow monitor and total fuel flow as measured by the fuel flow monitor and compares the ratio to a first plume presence value and produces a first input if the ratio is at least equal to the first plume presence value;

compares the opacity of the exhaust gasses as determined by the opacity monitor to a second plume presence value only if the first input is produced;

compares the carbon monoxide content of the exhaust gasses as determined by the carbon monoxide monitor to a third plume presence value only if the first input is produced; and compares the oxygen content of the exhaust gasses as determined by the oxygen monitor to a fourth plume presence value only if the first input is produced to produce a second input, a third input, and a fourth input, respectively, into the determination of the presence of a visible plume.

16. The system of claim 15, wherein the control system signals the presence of a visible plume at the stack of the facility if the ratio, the opacity, the carbon monoxide content, and the oxygen content indicate a visible plume.

17. The system of claim 16, wherein the combustion chamber combusts No. 6 fuel oil, the first plume presence value is 1.02 and the second plume presence value is 20 percent.

18. The system of claim 15, wherein the first plume presence value is generated from the ratio and at least one of carbon monoxide content of the exhaust gasses, oxygen content of the exhaust gasses, speed of an induced draft fan, weight of fuel being combusted, amount of natural gas being used, type of fuel being used, and electricity demand of the facility.

19. A control module for determining the presence of a visible plume of exhaust gasses at a power generation facility with a stack, that performs the steps of:

receiving as an input a total air flow value for air flow into a combustion chamber with excess air conditions during combustion;

receiving as an input a total fuel flow value for a fuel flow into the combustion chamber during combustion;

generating a plume presence signal including a ratio of total air flow to total fuel flow; and comparing the ratio to a first plume presence value to produce a first input into the determination of the presence of a visible plume if the ratio is at least equal to the first plume presence value.

20. The control module of claim 19, wherein the control module is receiving as an input a total fuel flow value for a fuel flow of No. 6 fuel oil into the combustion chamber during combustion; and comparing the ratio to a first plume presence value of 1.02 to produce the first input into the determination of the presence of a visible plume if the ratio is at least equal to 1.02.

21. The control module of claim 19, further comprising the steps of:

receiving as an input an opacity value for a flow of exhaust gasses from the combustion chamber during combustion; and comparing the opacity value to a second plume presence value to produce a second input into the determination of the presence of a visible plume at the stack of the facility only if the first input has been produced.

22. The control module of claim 21, further comprising the step of:

signaling the presence of a visible plume at the stack of the facility if the ratio and the opacity value indicate a visible plume.

23. The control module of claim 22, wherein the control module is receiving as an input a total fuel flow value for a fuel flow of No. 6 fuel oil into the combustion chamber during combustion;

comparing the ratio to a first plume presence value of 1.02 and producing the first input into the determination of the presence of a visible plume if the ratio is at least equal to 1.02; and comparing the opacity value to a second plume presence value of 20 percent to produce the second input into the determination of the presence of a visible plume at the stack of the facility only if the first input has been produced.

24. The control module of claim 19, further comprising the steps of:

receiving as an input a carbon monoxide content value for a flow of exhaust gasses from the combustion chamber during combustion;

receiving as an input an oxygen content value of the flow of exhaust gasses from the combustion chamber during combustion;

comparing the carbon monoxide content value to a second plume presence value to produce a second input into the determination of the presence of the visible plume only if the first input has been produced; and comparing the oxygen content value to a third plume presence value to produce a third input into the determination of the presence of the visible plume only if the first input has been produced.

25. The control module of claim 24, further comprising the step of:

signaling the presence of a visible plume at the stack of the facility if the ratio, the carbon monoxide content value, and the oxygen content value indicate a visible plume.

26. The control module of claim 25, further comprising the steps of:

receiving as an input value that is correlated to the power being generated by an electrical generator at the power generation facility; and determining as a function of the power being generated values for the second plume presence value and the third plume presence value only if the first input has been produced.

27. The control module of claim 26, wherein the control module is receiving as an input a total fuel flow value for a fuel flow of No. 6 fuel oil into the combustion chamber during combustion; and comparing the ratio to a first plume presence value of 1.02 to produce the first input into the determination of the presence of a visible plume if the ratio is at least equal to 1.02.

28. The control module of claim 19, wherein the first plume presence value is generated from the ratio and at least one of carbon monoxide content of the exhaust gasses, oxygen content of the exhaust gasses, speed of an induced draft fan, weight of fuel being combusted, amount of natural gas being used, type of fuel being used, and electricity demand of the facility.

29. A method of determining the presence of a visible plume of exhaust gasses at a power generation facility with a stack, comprising the steps of:
- determining a total air flow value for air flow into a combustion chamber with excess air conditions during combustion;
- determining a total fuel flow value for a fuel flow into the combustion chamber during combustion;
- generating a plume presence signal including a ratio of total air flow to total fuel flow; and
- comparing the ratio to a first plume presence value to produce a first input into the determination of the presence of a visible plume if the ratio is at least equal to the first plume presence value;
- signaling the presence of the visible plume to an operator.

30. The method of claim 29, wherein the total fuel flow value for a fuel flow of No. 6 fuel oil into the combustion chamber during combustion is determined; and
- the ratio is compared to a first plume presence value of 1.02 to produce the first input into the determination of the presence of a visible plume if the ratio is at least equal to 1.02.

31. The method of claim 29, further comprising the steps of:
- measuring an opacity value for a flow of exhaust gasses from the combustion chamber during combustion; and
- comparing the opacity value to a second plume presence value only if the first input has been produced.

32. The method of claim 31, further comprising the step of signaling the presence of a visible plume if the ratio and the opacity value indicate a visible plume.

33. The method of claim 32, wherein the total fuel flow value for a fuel flow of No. 6 fuel oil into the combustion chamber during combustion is determined;
- the ratio is compared to a first plume presence value of 1.02 to produce the first input into the determination of the presence of a visible plume if the ratio is at least equal to 1.02; and
- the opacity value is compared to a second plume presence value of 20 percent to produce a second input into the determination of the presence of a visible plume only if the first input is produced.

34. The method of claim 29, further comprising the steps of:
- determining a carbon monoxide content value of a flow of exhaust gasses from the combustion chamber during combustion;
- determining an oxygen content value of the flow of exhaust gasses from the combustion chamber during combustion;
- comparing the carbon monoxide content value to a second plume presence value only if the first input is produced; and
- comparing the oxygen content value to a third plume presence value only if the first input is produced.

35. The method of claim 34, further comprising the step of signaling the presence of a visible plume if the ratio, the carbon monoxide content value and the oxygen content value indicate a visible plume.

36. The method of claim 35, further comprising determining the second plume presence value and the third plume presence value as a function of the power being generated by an electrical generator at the power generation facility only if the first input is produced.

37. The method of claim 36, wherein the total fuel flow value for a fuel flow of No. 6 fuel oil into the combustion chamber during combustion is determined; and the ratio is compared to a first plume presence value of 1.02 and the first input is produced into the determination of the presence of a visible plume if the ratio is at least 1.02.

38. The method of claim 29, wherein the first plume presence value is generated from the ratio and at least one of carbon monoxide content of the exhaust gasses, oxygen content of the exhaust gasses, speed of an induced draft fan, weight of fuel being combusted, amount of natural gas being used, type of fuel being used, and electricity demand of the facility.

39. A method of determining the presence of a visible plume of exhaust gasses at a power generation facility with a stack, wherein the method comprises the steps of:
- determining a total air flow value for air flow into a combustion chamber with excess air conditions during combustion;
- determining a total fuel flow value for fuel flow into the combustion chamber during combustion;
- generating a plume presence signal including a ratio of total air flow to total fuel flow;
- measuring an opacity value for a flow of exhaust gasses from the combustion chamber during combustion;
- determining a carbon monoxide content value of a flow of exhaust gasses from the combustion chamber during combustion;
- determining an oxygen content value of the flow of exhaust gasses from the combustion chamber during combustion;
- comparing the ratio to a first plume presence value;
- comparing the opacity value to a second plume presence value only if the ratio is at least equal to the first plume presence value;
- comparing the carbon monoxide content value to a third plume presence value only if the ratio is at least equal to the first plume presence value; and
- comparing the oxygen content value to a fourth plume presence value only if the ratio is at least equal to the first plume presence value;
- signaling the presence of the visible plume to an operator.

40. The method of claim 39, further comprising the step of signaling the presence of a visible plume if the ratio, the opacity value, the carbon monoxide content value, and the oxygen content value indicate the presence of a visible plume.

41. The method of claim 40, further comprising determining the third plume presence value and the fourth plume presence value as a function of the power being generated by an electrical generator at the power generation facility if the ratio is at least equal to the first plume presence value.

42. The method of claim 41, wherein the total fuel flow value for a fuel flow of No. 6 fuel oil into the combustion chamber during combustion is determined;
- the ratio is compared to a first plume presence value of 1.02 to produce a first input into the determination of the presence of a visible plume if the ratio is at least 1.02; and
- the opacity value is compared to a second plume presence value of 20 percent to produce a second input into the determination of the presence of a visible plume if the first input has been produced.

43. The method of claim 39, wherein the first plume presence value is generated from the ratio at least one of carbon monoxide content of the exhaust gasses, oxygen content of the exhaust gasses, speed of an induced draft fan, weight of fuel being combusted, amount of natural gas being used, type of fuel being used, and electricity demand of the facility.

44. A system that determines the presence of a visible plume of exhaust gasses at a power generation facility with a stack, wherein the system comprises:

an air flow monitor that measures total air flowing into a combustion chamber during combustion;

a fuel flow monitor that measures total fuel flowing into the combustion chamber during combustion;

a mechanism that determines a ratio of total air flow as measured by the air flow monitor and the total fuel flow as measured by the fuel flow monitor and compares the ratio to a first predetermined value to produce a first input into the determination of the presence of a visible plume;

an exhaust path through which exhaust gasses are routed from the combustion chamber to the stack during combustion;

a carbon monoxide monitor located in one of the stack and the exhaust path that determines the carbon monoxide content of the exhaust gasses;

an oxygen monitor located in one of the stack and the exhaust path that determines the oxygen content of the exhaust gasses;

wherein the mechanism compares the carbon monoxide content of the exhaust gasses as determined by the carbon monoxide monitor to a second predetermined value and compares the oxygen content of the exhaust gasses as determined by the oxygen monitor to a third predetermined value to produce a second input and a third input, respectively, into the determination of the presence of a visible plume;

wherein the mechanism signals the presence of a visible plume if the ratio, the carbon monoxide content of the exhaust gasses, and the oxygen content of the exhaust gasses indicate a visible plume;

a boiler to provide steam to a steam turbine; the boiler heated by heat from combustion of a fuel in the combustion chamber of the boiler; the steam turbine driven by steam from the boiler; the steam turbine drivingly connected to an electrical power generator for the generation of electrical energy;

an energy monitoring device for measuring the electrical energy being generated by the generator; and wherein the mechanism continuously determines the second predetermined value and the third predetermined value as functions of the electrical energy being generated by the generator, as such electrical energy is measured by the energy monitor, and as a function of the fuel.

45. The system of claim 44, wherein the fuel is No. 6 fuel oil.

46. The system of claim 45, wherein the first predetermined value is 1.02.

47. A system that determines the presence of a visible plume of exhaust gasses at a power generation facility with a stack, wherein the system comprises:

an air flow monitor that measures total air flowing into a combustion chamber during combustion;

a fuel flow monitor that measures total fuel flowing into the combustion chamber during combustion;

a control system that determines a plume presence signal including a ratio of total air flow as measured by the air flow monitor and the total fuel flow as measured by the fuel flow monitor and compares the ratio to a first plume presence value to produce a first input into the determination of the presence of a visible plume if the ratio is at least equal to the first plume presence value;

an exhaust path through which exhaust gasses are routed from the combustion chamber to the stack during combustion;

a carbon monoxide monitor located in one of the stack and the exhaust path that determines the carbon monoxide content of the exhaust gasses;

an oxygen monitor located in one of the stack and the exhaust path that determines the oxygen content of the exhaust gasses;

wherein the control system compares the carbon monoxide content of the exhaust gasses as determined by the carbon monoxide monitor to a second plume presence value and compares the oxygen content of the exhaust gasses as determined by the oxygen monitor to a third plume presence value to produce a second input and a third input, respectively, into the determination of the presence of a visible plume;

wherein the control system signals the presence of a visible plume if the ratio, the carbon monoxide content of the exhaust gasses, and the oxygen content of the exhaust gasses indicate a visible plume;

a boiler to provide steam to a steam turbine, the boiler heated by heat from combustion of a fuel in the combustion chamber of the boiler, the steam turbine driven by steam from the boiler, the steam turbine drivingly connected to an electrical power generator for the generation of electrical energy, and an energy monitoring device for measuring the electrical energy being generated by the generator; and wherein the control system continuously determines the second plume presence value and the third plume presence value as functions of the electrical energy being generated by the generator, as such electrical energy is measured by the energy monitor, and as a function of the fuel.

48. The system of claim 47, wherein the fuel is No. 6 fuel oil.

49. The system of claim 47, wherein the first plume presence value is 1.02.

* * * * *